United States Patent [19]

Meguro et al.

[11] Patent Number: 4,677,372
[45] Date of Patent: Jun. 30, 1987

[54] CUVETTE BELT FAULTY SEAL DETECTOR

[75] Inventors: Jun-Ichi Meguro, Huntington Beach; Kelvin O. McKisic, Los Angeles; James R. Manley, Jr., Costa Mesa, all of Calif.

[73] Assignee: American Hospital Supply Corp., Evanston, Ill.

[21] Appl. No.: 746,172

[22] Filed: Jun. 18, 1985

[51] Int. Cl.⁴ ............................................. G01R 31/12
[52] U.S. Cl. ........................................ 324/54; 204/401
[58] Field of Search ............... 324/54, 52, 51, 72.5; 340/647; 422/66, 65; 73/52; 204/401

[56] References Cited

U.S. PATENT DOCUMENTS

| | | | |
|---|---|---|---|
| 1,427,817 | 9/1922 | Hutchinson | 324/54 X |
| 3,543,924 | 12/1970 | Ryan et al. | 324/54 X |
| 4,528,159 | 7/1985 | Liston | 422/65 |

Primary Examiner—Reinhard J. Eisenzopf
Assistant Examiner—Jack B. Harvey
Attorney, Agent, or Firm—Perman & Green

[57] ABSTRACT

A system for testing plastic cuvette belts for leak holes in the cuvettes comprises an array of conductive probes which are inserted into respective ones of a group of adjacent cuvettes. Alternate probes are biased to opposite high potentials sufficient to create arcing between the probes through any faulty seal in the cuvettes. A grounded electrode outside the cuvette enables holes to the outside to be detected also.

6 Claims, 10 Drawing Figures

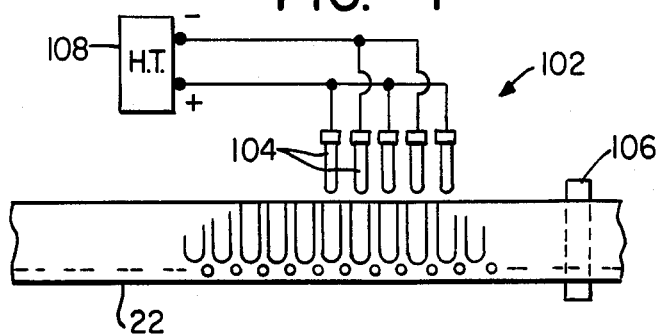
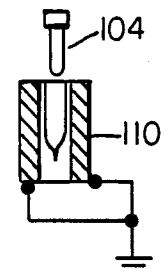
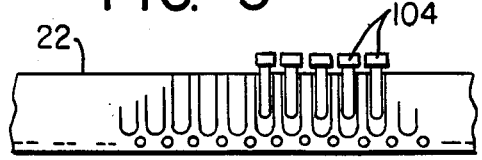
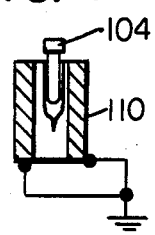
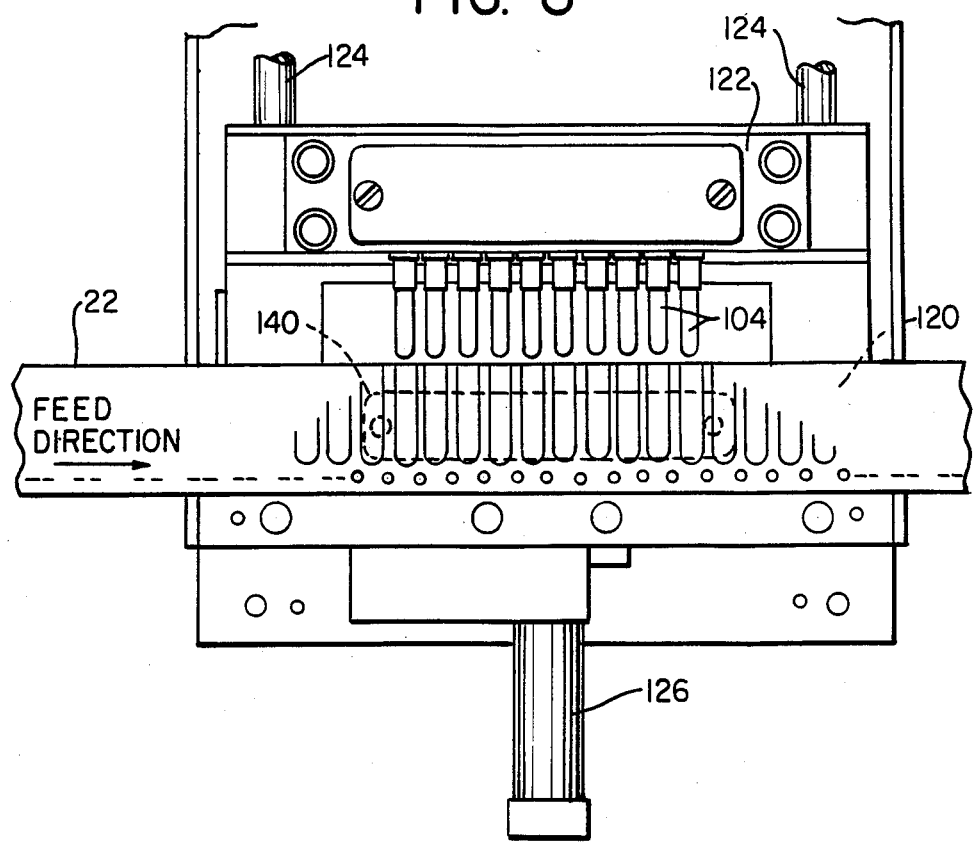

CUVETTE BELT FAULTY SEAL DETECTOR

INTRODUCTION

The present invention is concerned generally with cuvettes for use in the chemical analysis of fluid samples in an automated instrument and more particularly to flexible cuvette belts consisting of a plurality of integrally interconnected cuvettes which are designed to be transported through such an instrument. The invention relates to apparatus for detecting faulty seals, such as leaks, in the cuvettes of such cuvette belt and particularly to such apparatus which is adapted for automatic operation.

BACKGROUND OF THE INVENTION

A variety of automated or semi-automated chemical analyzers are known which utilize cuvettes for the chemical testing of samples placed therein. Generally a predetermined amount of liquid sample, such as biological fluid, is placed in the cuvette which is then transported through the instrument. As the cuvette is being transported, the instrument dispenses a quantity of reagent into the sample and monitors the resulting chemical reaction. Such monitoring is generally accomplished through use of an optical means which views the fluid sample through optically transparent portions of the cuvette.

In order to simplify the loading of the cuvettes into the instrument and facilitate their handling by the instrument once so loaded, proposals have been made to provide the cuvettes in the form of a continuous integral strip. The individual cuvettes of the strip are designed to be relatively rigid but the strip itself is provided with sufficient flexibility to ease its transport through the instrument. Furthermore, by making the cuvettes in continuous strip form, they can be manufactured relatively inexpensively from suitable plastic material thereby permitting their disposal after sue. This is an important feature since it avoids the requirements for washing the cuvettes after use and avoids any possibility of crosscontamination of fluid samples which could cause erroneous test results. A proposed cuvette system designed to meet these requirements is disclosed in U.S. Pat. No. 4,263,256.

In commonly owned copending U.S. patent application Ser. No. 559,016 filed Dec. 8, 1983 entitled "Cuvette System For Automated Chemical Analyzer", a continuation of U.S. patent application Ser. No. 284,842 filed July 20, 1981, the disclosure of which is hereby incorporated by reference in its entirety herein, there is described a cuvette belt which comprises a matching pair of elongated, formed plastic strips which are joined together along corresponding faces thereof to form an integral belt. A series of regularly spaced chamber halves are formed transversely in each of the corresponding strip faces which define open-topped cuvette receptacles when the belt halves are joined.

As described, the cuvette belt is made by forming strip plastic material with a series of regularly spaced transverse (laterally extending) formed pockets so as to define two integral side-by-side belt halves. The formed strip is then divided longitudinally to separate the belt halves and the belt halves brought into register and joined together to form a completed cuvette belt.

Reference is also made to commonly owned copending U.S. patent application Ser. No. 746,231 filed June 18, 1985, entitled "Cuvette Belt Manufacture and Process", the disclosure of which application is hereby incorporated by reference in its entirety herein. In that application is disclosed an alternative method for making cuvette belts of the kind comprising a matching pair of plastic strips, each of which is formed with chamber halves and which are joined together to form an integral cuvette belt with the chamber halves aligned to form the cuvettes.

According to that method, two strips of plastic material are identically formed with a series of regularly spaced transverse formed pockets so as define two integral side-by-side mirror image belt halves. The two formed strips are brought into register and joined together to form a composite strip defining two integral mirror image cuvette belts joined together by their cuvette mouth ends. The composite strip is then divided longitudinally to separate the cuvette belts.

The present invention is concerned with a method of testing cuvette belts which is applicable to such belts in general while having particular applicability to the kinds of belts disclosed in the aforesaid copending applications.

SUMMARY OF THE INVENTION

Accordingly, the present invention provides a method and apparatus for testing plastic cuvette belts for faulty seals, such as leak holes in the cuvettes in which at least two conductive probes are inserted into adjacent cuvettes. Adjacent probes are biased to opposite potentials sufficient to cause arcing or current flow between the probes through any faulty seals, such as leak holes, between the adjacent cuvettes.

In a preferred form of the invention, a grounded electrode is provided outside the cuvettes, in which case the probe potentials must also be sufficient to cause arcing between a probe and the grounded electrode through any faulty seal extending through the cuvette to the outside.

Such a system lends itself to automation and an automated embodiment of test apparatus according to the invention includes means for advancing a cuvette belt in steps to align successive groups of cuvettes with an array of probes. The probe array is adapted for inserting the probes into cuvettes which have been aligned with the array. Adjacent probes in the array are biased to opposite potential sufficient to cause arcing or current flow between the probes through any faulty seal between adjacent cuvettes. In order to assure that leaks between the end ones of adjacent cuvette groups are tested for, the belt advancing means is adapted to advance the belt by a number of cuvettes equal to one less than the number of probes.

DESCRIPTION OF THE DRAWINGS

Other features and advantages of the present invention will become apparent from the following description taken in conjunction with the accompanying drawings wherein:

FIGS. 4 and 5 are schematic side views illustrating the principles of operation of a faulty seal detector according to the present invention, respectively, showing the probes thereof in their retracted and inserted positions, FIGS. 6 and 7 are schematic end views corresponding to the side views of FIGS. 4 and 5, respectively, FIG. 8 is a top view of one-half of an embodiment of the faulty seal detector as utilized in the equipment of FIG. 1.

DESCRIPTION OF THE PREFERRED EMBODIMENTS

Figure 1:
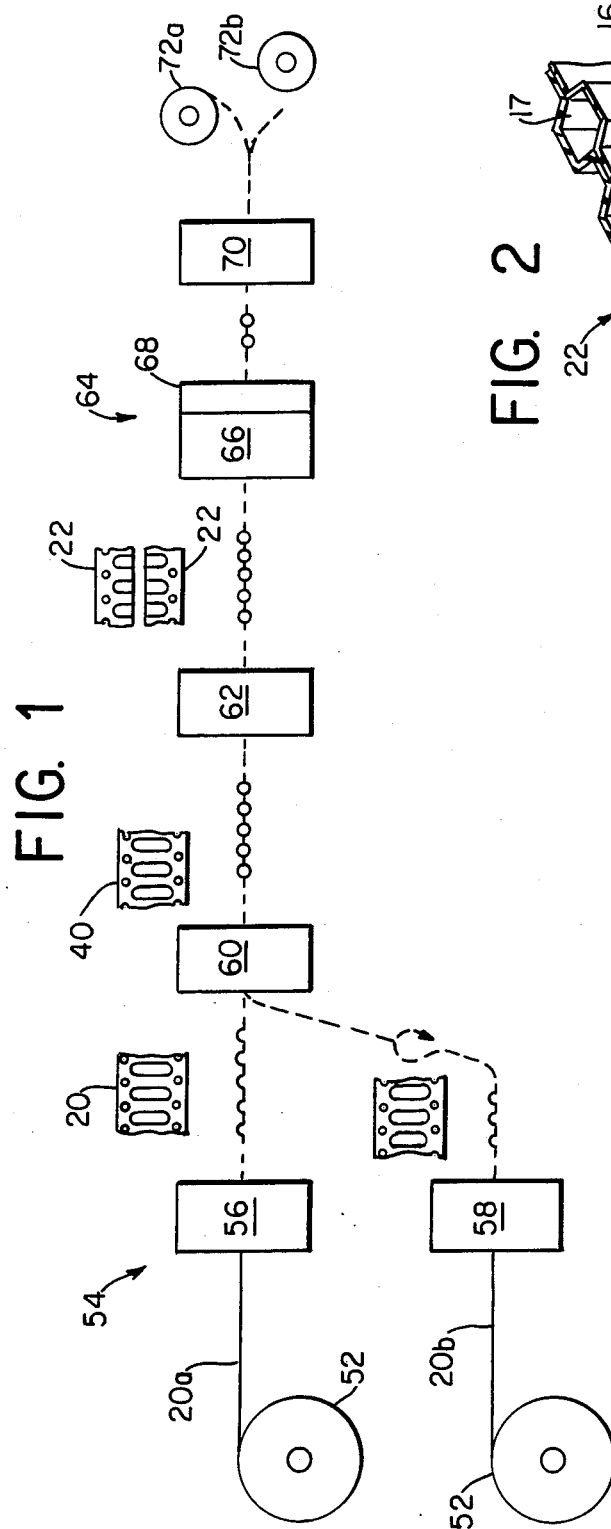
FIG. 1 is a diagrammatic side elevational view of an embodiment of automatic equipment for making cuvette belts from strip plastic material incorporating a faulty seal detector according to the present invention.
Figure 2:
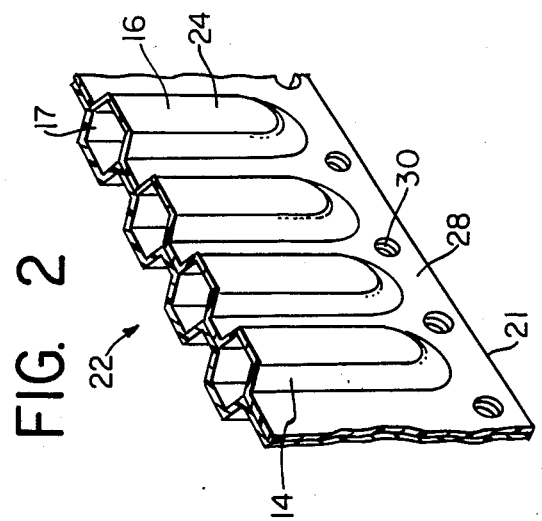
FIG. 2 is a perspective view of a cuvette belt made on the equipment shown in FIG. 1.
Figure 3:
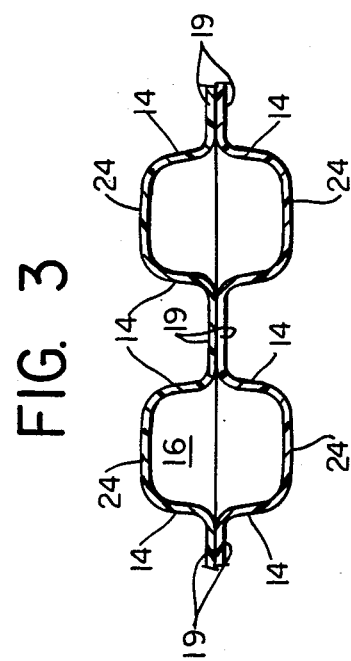
FIG. 3 is a horizontal cross section through the cuvette belt.

Referring to the drawing, FIG. 1 illustrates schematically an embodiment of an automatic system for producing plastic cuvette belts as shown in FIGS. 2 and 3 which includes a faulty seal detector according to the present invention. Such automatic cuvette making system is described in detail in our aforesaid copending U.S. patent application Ser. No. 746,231 filed June 18, 1985 entitled "Cuvette Belt Manufacturing Apparatus and Process". However, such system is only described in outline herein to the extend necessary for an understanding of the subject of the present invention and for a detailed understanding of that system reference should be had to the aforesaid copending patent application.

Referring now to FIG. 1 the system shown produces cuvette belts from strip plastic material which is advanced in turn to an in-line series of processing stations to produce the completed belts. The system illustrated simultaneously forms two cuvette belts from two strips 20a, 20b of plastic material.

Each strip 20 is supplied from a reel 52 and advanced to a forming station 54 where it is formed in a respective forming press 56, 58 with a series of regularly spaced, shallow transverse pockets 17 having sidewalls 14 so as to define two integral side-by-side mirror image belt halves. At the same time a line of indexing perforations 30 is formed along each side edge of the strip. These perforations 30 are utilized by clinical analyzer to precisely control the transport of the cuvette belts through the analyzer. The perforations may also be used in the cuvette manufacturing illustrated for driving the formed strips there through for subsequent processing and in particular for accurately aligning the strips when they are brought together for joining as will now be described.

After they leave their respective forming presses 56, 58, the two formed strips 20 are brought together in precise face-to-face registration and joined together at a heat sealing station 60 to form a composite strip 40 defining two integral side-by-side mirror image cuvette belts 22. If the lower strip 20b is formed the same way up as the upper strip 20a as shown, then it is twisted through 180° on its way to the sealing station so that when the two strips are brought together the pockets together define closed chambers.

The composite strip leaving the heat sealer 60 is advanced to a slitting station 62 where it is slit longitudinally along its center line to separate the cuvette belts 22. The two completed cuvette belts 22 formed, as shown in FIGS. 2 and 3, comprise a series of open-topped chambers separated by thin web portions 19 having a web-like transport area 28 on its lower edge having the indexing perforations formed therein. The belts 22 are generally rectangular in cross-section and their side walls 24 define optical windows to facilitate photoanalysis of samples in the cuvettes.

It has been found that copolyester or vinyl plastic strip stock in the thickness of about 0.005 to about 0.010 inch provides satisfactory optical qualities for use in the manufacture of cuvette belts of the kind discussed herein. A suitable example of such a material is KODAR brand Thermoplastic Co. Polyester Resin manufactured by Eastman Chemical, Rochester, N.Y. In order to facilitate the fabrication and assembly of the cuvette belt, the strip stock is preferably a laminate, having a layer of easily sealable, biologically inert material, such as SURLYN brand Ionomer Resin material manufactured by E.I. duPont de Nemours, & Co., Inc., Wilmington, Del., along the face of the strip which contacts the matching strip to which it is joined.

The formed strips 20 may be joined together by a low heat sealing process if a laminate material such as SURLYN is utilized as described above or by impulse bonding techniques if higher melting point materials are utilized. It is also possible to utilize other joining methods, such as adhesive bonding, as long as the optical characteristics and dimensional tolerances of the cuvettes are not adversely affected thereby.

It will be appreciated from the foregoing that the cuvette belts 22 are composed of two belt halves, each having a series of chamber halves formed therein joined together by sealing them around the chambers of the web portions 19 and in the transport area 28. The integrity of the individual cuvettes 16 thus depends in particular upon the accuracy of strip alignment at the sealing station 60 as well as the effectiveness of the sealing process itself.

Since such belts are intended for use in chemical analysis equipment it is vitally important that there be no leakage between the cuvettes which would lead to cross-contamination. It is important to avoid leaks in the cuvettes to the ouside as well, as these may result in spillage of the cuvette contents. It is important therefore that the cuvette belt be checked for leaks including nearly imperceptible "pin holes", and to this end the cuvette belts leaving the slitting station pass to an inspection station 64.

The inspection station 64 includes a faulty seal detector, or high voltage leak detector, 66 according to the present invention which is described in detail below. Associated with the leak detector 66 is a marking device 68 which is responsive to the detection of a faulty of leaky cuvette by the leak detector to cause a mark to be applied to the faulty cuvette. This mark is preferably machine readable so that it can be read at a cutting station 70 arranged following the inspection station 64 to cause the cuvette belt 22 to be cut ahead of and behind the faulty cuvette to remove it from the cuvette belt before it is wound on storage spools 72a and 72b. Preferably the cutting station includes a counter which counts a predetermined number of cuvettes following a faulty cuvette before effecting the second cut to avoid unnecessary operation of the cutter in the event of a faulty length of cuvette belt occurring.

If desired the inspection station 64 may include a visual inspection check also associated with a marking device.

Turning now to the specific subject of this invention, a high voltage leak detector apparatus suitable for use in the system shown in FIG. 1 will now be described with reference to FIGS. 5–10. It comprises an array 102 of conductive probes 104 and an indexing drive 106 for advancing a cuvette belt 22 stepwise past the probe array 102 for aligning successive groups of cuvettes with the array. The probes 104 are mounted for movement towards and away from the belt for insertion of the probes into the cuvettes (FIGS. 6 and 7) and for their retraction (FIGS. 4 and 5) following a test cycle and during advance of the cuvette belt 22. The probes 104 are connected to a high voltage power supply 108 and alternate probes 104 are respectively positively and negatively biased. The biasing potentials of the probes should be sufficient to cause arcing or current flow between the probes through and faulty seal in adjacent cuvettes.

Surrounding the cuvette belt in the leak detector is a grounded electrode 110 which is profiled closely to fit around the sides and base of the cuvette belt. This electrode 110 enables leak holes extending through the cuvette to the outside to be detected by making the probe potential sufficient to cause arcing or current flow between the probe 104 and the grounded electrode 110.

It has been found that a probe potential of about plus or minus 15,000 volts is particularly effective for detecting faulty seals, pin holes, leaks, etc. in a cuvette belt 22. However other voltages may be applied and voltages in the range of about plus or minus 12,000 to 30,000 volts would be suitable under some conditions.

In FIGS. 4–7, an array of five probes 104 is shown. It will be understood that if the cuvette belt is indexed in steps of the same number (5) of cuvettes that there will be no check for leaks between the last cuvette in one group and the first cuvette in the next group. For this reason the cuvette belt is preferably advanced stepwise by a number of cuvettes equal to at least one less than the number of probes. In this case the belt is advanced in steps of four cuvettes.

Figure 9:
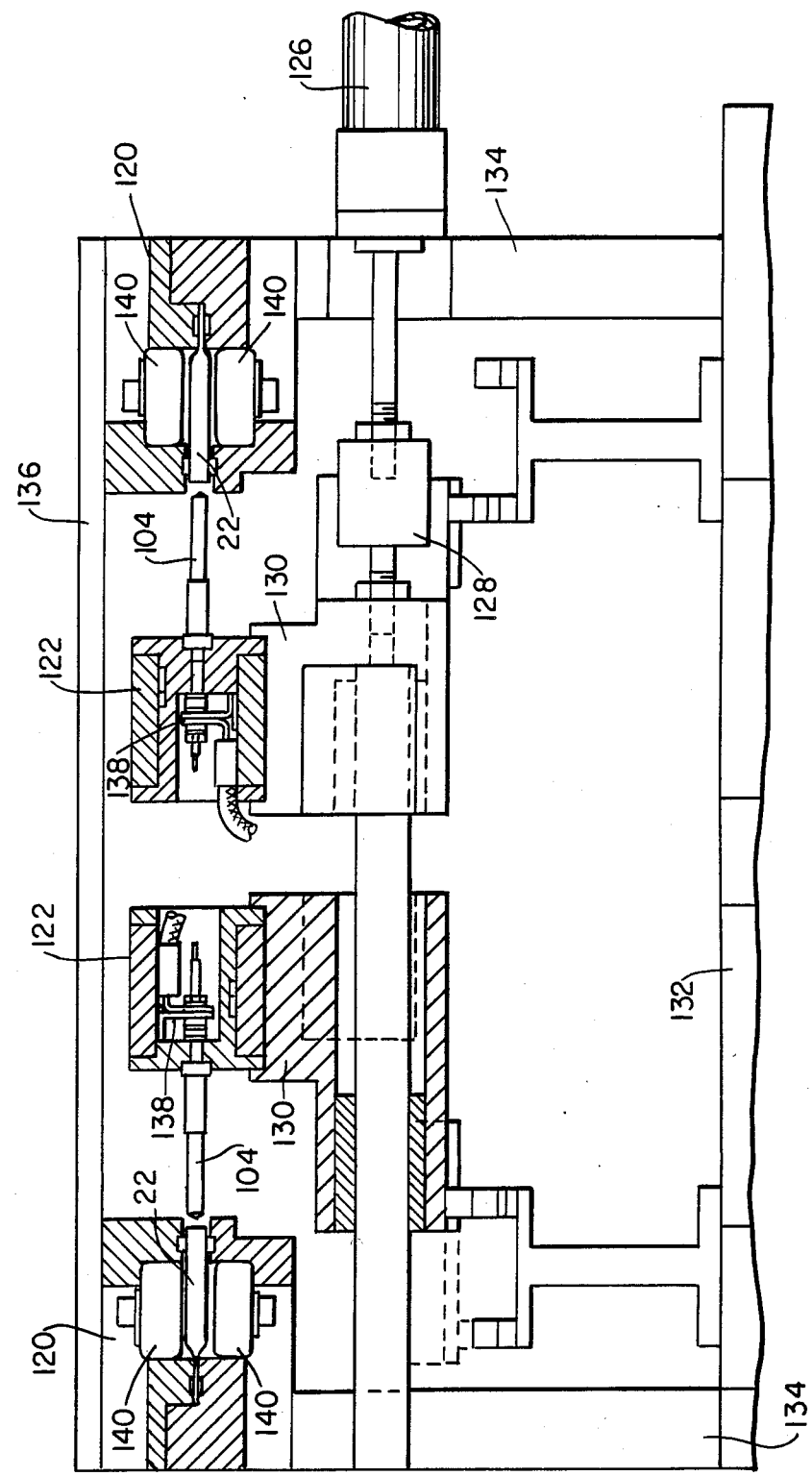
FIG. 9 is a side elevation, partly in section of the entire apparatus shown partly in FIG. 8.
Figure 10:
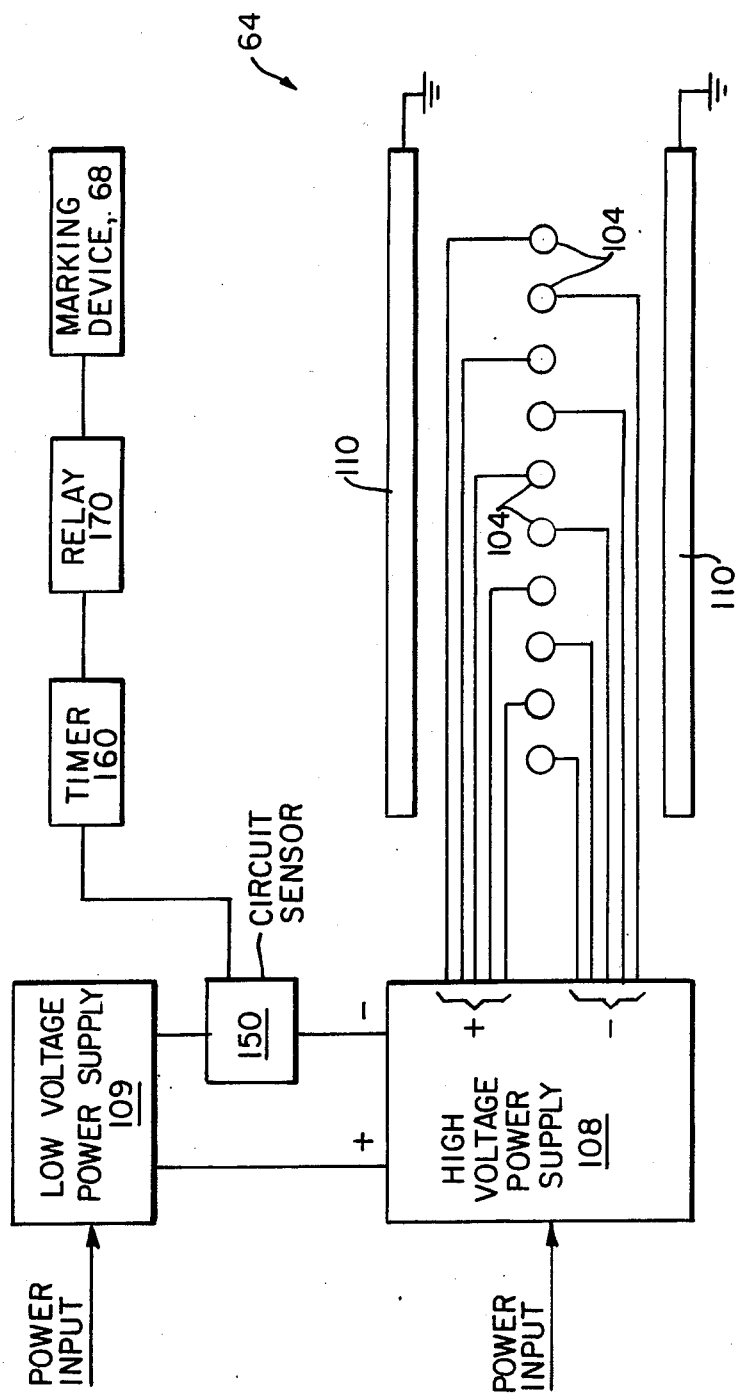
FIG. 10 is a schematic diagram of a system that detects faulty seals and activates the marking device.

The embodiment of leak detector shown in FIGS. 8–10 is particularly adapted for use in the belt manufacturing system shown in FIG. 1 and includes two back-to-back arrays of probes as particularly seen in FIG. 9. The cuvettes 22 are guided through fixed guide blocks 120 and the probes 104 are carried on probe mounting blocks 122 which are slidably mounted on a pair of slide rods 124 for movement towards and away from the guide blocks 120 for insertion into and withdrawal from the cuvettes 22 of the probes 104. Movement of the probe mounting blocks 122 is by means of air cylinder 126 through linkages 128 (only one of which is shown), the mounting blocks 122 being supported off the slide rods 124 on slide bars 130. The whole arrangement is mounted off a base plate 132 on side plates 134. A clear plexiglass top safety cover 136 is provided over the probes.

A cuvette is illustrated in dotted outline and its position in each of the guide blocks 120 and the probes 104 are shown in full lines in their retracted positions while the left hand probe 104 is also shown in dotted outline in its inserted position. The probes 104 are securely held in the mounting blocks 122 and each mounting block 122 carries two bus bars 138 (only one of which is shown in each case) by which the negative and positive high tension leads are respectively connected to the probes 104.

The guide blocks 120 for the cuvettes each include two grounded contact plates 140 one at each side of the cuvette belt 22 which serve as the grounded electrode.

In the belt making system of FIG. 1, the strips 20 are formed and sealed in batches of 8 cuvettes and in order to match the speed of the leak detector 66 to the rest of the system, the cuvette belts 22 are advanced therethrough in groups of eight cuvettes. For this purpose 10 probes are provided in each detector.

FIG. 10 is a schematic electrical diagram of a control system that detects when a faulty seal exists and activates the marking device 68 to flag it. High voltage power supply 108 is fed from a suitable power source, or input, and supplies suitable voltages, such as plus and minus 15,000 voltages, to the probes 104. The electrodes 110 are grounded so that, in this embodiment, the potential difference between each probe and each ground plate is 15,000 volts while the potential difference between two adjacent probes is 30,000 volts. A low voltage D.C. power supply 109 (28 volts), fed by a suitable power input, is connected to the high voltage power supply 108 so that current sensor 150 detects when arcing between two adjacent probes or a probe and electrode 110 occurs. The current sensor is connected to a timer 160 which is connected to relay 170. The relay is connected to marking device 68.

The detection of an arc in the inspection station by current sensor 150 activates timer 160 which activates relay 170 for a given period of time, the period being equivalent to the time for the marking device to be carried through one marking cycle. Upon completion of the marking cycle, timer 160 is reset so that it can be activated again by current sensor 150 when the next arcing occurs in a subsequent section of cuvettes in inspection station 64. Thus, for each detection of an arc, or faulty seal, the marking device 68 is activated to mark that section of cuvettes in the inspection station as defective. It is understood that the detection system may optionally be implemented by a microprcessor.

Current sensor 150 may optionally have a lamp, alarm or some other means to indicate that a faulty seal is present to the operator. Also, marking device 68 may be located downstream of inspection station 64 and timer 160 can be designed to delay the marking cycle when a defect is found to exist until the section of cuvettes having the defect is indexed downstream of the inspection station. Preferably, the voltage applied to probe 104 is applied only during the time the probes are fully inserted into the cuvettes. The marking device can apply a machine readable mark to the faulty cuvettes which is subsequently read and acted upon at the cutting station as previously described. The power supplies, current sensor, timer, relay and marking device can be of any suitable type and each such element is well known in the art.

Although particular configurations and features of the present invention have been discussed in connection with the above described preferred embodiments thereof, it should be understood that those skilled in the art may make various changes, modifications and substitutions thereto without departing from the spirit and scope of the invention as defined in the appended claims.

What is claimed is:

1. Apparatus for testing plastic cuvette belts for faulty seal in the cuvettes, said cuvettes having separator portions therebetween, the apparatus comprising at least two conductive probes, means for inserting the probes into adjacent cuvettes and means for biasing adjacent said probes to opposite potentials sufficient to cause arcing between said probes through any faulty seal in said separator portions between said adjacent cuvettes.

2. Test apparatus as defined in claim 1 including grounding means outside said cuvettes, said probe potentials being sufficient to cause arcing between a said probe and said grounding means through any faulty seal extending through a cuvette to the outside.

3. Apparatus for testing plastic cuvette belts for faulty seals in the cuvettes, said cuvettes having separator portions therebetween, the apparatus comprising a plurality of probes, means for advancing a cuvette belt in steps to align successive pluralities of cuvettes with said probes, means for inserting said probes in said cuvettes aligned therewith, and means for biasing adjacent said probes to opposite potentials sufficient to cause arcing between said probes through any faulty seal in said separator portions between adjacent cuvettes, said cuvette belt advancing means being adapted to advance said belt by a number of cuvettes equal to one less than the number of probes.

4. Test apparatus as defined in claim 3 including a grounded electrode at each side of said cuvette belt, said probe potentials being sufficient to cause arcing between a said probe and said grounded electrode through any faulty seal extending through a cuvette to the outside.

5. Test apparatus as defined in claim 3 including means for sensing the occurrence of said arcing.

6. Test apparatus as defined in claim 3 including marking means responsive to the occurrence of said arcing which is adapted to mark a faulty cuvette.

* * * * *